United States Patent
Sachdeva et al.

(10) Patent No.: US 11,911,501 B1
(45) Date of Patent: Feb. 27, 2024

(54) BIOCOMPATIBLE RESIN COMPOSITION AND METHOD OF MANUFACTURING DISSOLVABLE MICRONEEDLES FOR TRANSDERMAL DELIVERY USING BIOCOMPATIBLE RESIN

(71) Applicant: Florida A&M University, Tallahassee, FL (US)

(72) Inventors: Mandip Sachdeva, Tallahassee, FL (US); Arvind Bagde, Tallahassee, FL (US); Satyanarayan Dev, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 108 days.

(21) Appl. No.: 17/444,435

(22) Filed: Aug. 4, 2021

Related U.S. Application Data

(60) Provisional application No. 63/060,916, filed on Aug. 4, 2020.

(51) Int. Cl.
*A61M 37/00* (2006.01)
*A61K 9/00* (2006.01)
(Continued)

(52) U.S. Cl.
CPC .......... *A61K 9/0021* (2013.01); *A61K 31/192* (2013.01); *A61K 31/277* (2013.01);
(Continued)

(58) Field of Classification Search
CPC .. A61K 9/0021; A61K 31/192; A61K 31/277; A61M 37/0015;
(Continued)

(56) References Cited

U.S. PATENT DOCUMENTS

2023/0200966 A1* 6/2023 Romot .................... A61L 27/26
623/23.74

OTHER PUBLICATIONS

Van Landuyt et al., Evaluation of cell responses toward adhesives with different photoinitiating systems. Dental materials. 2015. vol. 31: 916-927.
(Continued)

*Primary Examiner* — Amber R Stiles
(74) *Attorney, Agent, or Firm* — Owen G. Behrens; Paul Murty; Smith & Hopen, P.A.

(57) ABSTRACT

A biocompatible resin composition that is used in the manufacture of a dissolvable microneedle that is used for the transdermal delivery of one or more active pharmaceutical ingredients to a subject. The biocompatible resin composition includes lithium phenyl-2,4,6-trimethylbenzoylphosphinate, water, and poly(ethylene glycol) diacrylate (molecular weight 550), and may include methacrylated hyaluronic acid, that is capable of forming a structurally stable microneedle patch. The microneedle patch is formulated with the biocompatible resin composition using a continuous, one-step process utilizing additive manufacturing. Once manufactured, the microneedle patches are formulated to adhere to an outer layer of a subject's skin. Once administered to the subject, the microneedle compositions create microscopic pathways into the subject's subdermal layers to deliver one or more active agents to the subject, such as to the subject's bloodstream.

9 Claims, 14 Drawing Sheets

(51) Int. Cl.
*A61K 31/192* (2006.01)
*A61K 31/277* (2006.01)
*B33Y 70/00* (2020.01)
*B33Y 80/00* (2015.01)

(52) U.S. Cl.
CPC ......... *A61M 37/0015* (2013.01); *B33Y 70/00* (2014.12); *B33Y 80/00* (2014.12); *A61M 2037/0023* (2013.01); *A61M 2037/0053* (2013.01); *A61M 2037/0061* (2013.01)

(58) Field of Classification Search
CPC .. A61M 2037/0023; A61M 2037/0053; A61M 2037/0046; A61M 2037/0061; B33Y 70/00; B33Y 80/00
See application file for complete search history.

(56) References Cited

OTHER PUBLICATIONS

Fairbanks et al., Photoinitiated polymerization of PEG-diacrylate with lithium phenyl-2, 4, 6-trimethylbenzoylphosphinate: polymerization rate and cytocompatibility. Biomaterials. 2009. vol. 30: 6702-6707.
Lin et al., Application of visible light-based projection stereolithography for live cell-scaffold fabrication with designed architecture. Biomaterials. 2013. vol. 34 (No. 2): 331-339.

* cited by examiner

| Batch | Methacrylated hyaluronic acid (Me HA) (% w/w) | Lithium phenyl-2,4,6-trimethylbenzoylphosphinate (LAP) (% w/w) | Water (% w/w) | Poly(ethylene glycol) diacrylate (PEGDAMA) (% w/w) |
|---|---|---|---|---|
| A1 | - | 0.25 | - | <99.75 |
| A2 | - | 0.5 | - | <99.5 |
| A3 | - | 0.5 | 16 | <83.5 |
| A4 | - | 0.75 | 20 | <79.25 |
| A5 | 0.25 | 0.25 | 16 | <83.5 |
| A6 | 0.50 | 0.50 | 16 | <83 |
| A7 | 0.75 | 0.75 | 20 | <78.5 |

Fig. 2

| Batch | Ibuprofen (% w/w) | Lithium phenyl-2,4,6-trimethylbenzoylphosphinate (LAP) (% w/w) | Water (% w/w) | Poly(ethylene glycol) diacrylate (PEGDAMA) (% w/w) |
|---|---|---|---|---|
| B1 | 8 | 0.225 | 10 | <81.775 |
| B2 | 8 | 0.225 | 20 | <71.775 |
| B3 | 8 | 0.225 | 30 | <61.775 |
| B4 | 8 | 0.49 | 10 | <81.51 |
| B5 | 8 | 0.49 | 20 | <71.51 |
| B6 | 8 | 0.49 | 30 | <61.51 |
| B7 | 8 | 0.75 | 10 | <81.25 |
| B8 | 8 | 0.75 | 20 | <71.25 |
| B9 | 8 | 0.75 | 30 | <61.25 |

Fig. 5

| Flux (μg/cm²/hr) Ibuprofen Microneedle Patch having 0.225% (w/w) LAP and 10% (w/w) water | 0-24 Hours | 24-48 Hours | 48-72 Hours |
|---|---|---|---|
| | 15.79 ± 0.92 | 19.63 ± 2.46 | 20.50 ± 4.05 |

Fig. 11

BIOCOMPATIBLE RESIN COMPOSITION AND METHOD OF MANUFACTURING DISSOLVABLE MICRONEEDLES FOR TRANSDERMAL DELIVERY USING BIOCOMPATIBLE RESIN

CROSS-REFERENCE TO RELATED APPLICATIONS

This nonprovisional application is a continuation of and claims priority to provisional application No. 63/060,916, entitled "Biocompatible resin formulation for the manufacturing of dissolvable microneedles for transdermal delivery using 3D printing," filed on Aug. 4, 2020, by the same inventors.

BACKGROUND OF THE INVENTION

1. Field of the Invention

This invention relates, generally, to biocompatible resins and to methods of topically delivering therapeutics via dissolvable microneedles. More specifically, it relates to a biocompatible resin composition that is capable of being manufactured via additive manufacturing into a dissolvable microneedle that is used in transdermal delivery of pharmaceutical formulations through the skin.

2. Brief Description of the Prior Art

Microscopic applicators, such as microneedles, have been used for years as a method of delivering various medicines and substances to the body through transdermal, intraocular, intracochlear, and similar delivery application sites. Such microscopic applicators include singular microneedles or an array of microneedles that are disposed on a patch or a similar delivery mechanism that is designed to reside on an outer layer of a subject's skin. The singular or array of microneedles then penetrate the outer layer of the skin, creating microscopic pores that act as channels from the surface of the skin to subdermal layers. As such, the microscopic pores provide pathways for pharmaceutical ingredients, such as therapeutic formulations, to traverse through the outer layer of skin and into the subject's bloodstream that reside in the lower dermal layers.

In the past, traditional microneedles were primarily fabricated using a multistep polydimethylsiloxane (PDMS) micromolding approach. In such methods, PDMS is used because it is thermally stable, flexible, non-hygroscopic, inert under physiological conditions, mechanically firm, and optically transparent. However, the multistep nature of the PDMS technique results in reproducibility issues and errors in the final product.

Accordingly, due to recent enhancements to additive manufacturing technologies, many medical devices, including microneedles and microneedle patches, are manufactured via 3D printing. Utilizing 3D printing technology for manufacturing microneedles has several benefits, including increased efficiency, high-throughput processing, increased accuracy, increased reproducibility, and single-step production. However, to produce structures via 3D printing, a suitable printing material must be used that can withstand the heating and cooling temperature cycles used in the extrusion and curing of a final additive manufactured product. Particularly because microneedles are used in therapeutic delivery systems, ensuring that the resin is biocompatible, stable, and effective at the creation of microscopic channels beneath the skin surface is of paramount importance. Moreover, due to the nature of inserting microneedles into a subject's outer skin layer and the creation of microscopic subdermal pathways, it is desirable that a biocompatible resin be capable of dissolving over time to prevent the need to dislodge a patch from the skin, which could result in increased risk of infection and other complications.

To date, the methods of manufacturing dissolving microneedles are typically accomplished using diphenyl(2, 4,6-trimethylbenzoyl)phosphine oxide (TPO) as a photoinitiator. The TPO is used in combination with poly(ethylene glycol) diacrylate (PEGDAMA), polycaprolactone, and polyacrylic acid using one-step 3D printing techniques. However, the use of TPO in therapeutic deliver has been shown to cause toxicity in clonal SV 40 large T-antigen transfected human pulp-derived cells (tHPC) [1]. As such, the use of TPO is not ideal for therapeutic delivery.

Recently, studies have shown that lithium phenyl-2,4,6-trimethylbenzoylphosphinate (LAP) is a biocompatible photoinitiator [2][3]. However, LAP has not been shown in the prior art to be used in combination with therapeutic delivery, such as via a microscopic applicator. Accordingly, what is needed is a biocompatible resin containing LAP as a photoinitiator using 3D printing technology to manufacture dissolvable microneedle patches that are capable of delivering active pharmaceutical ingredients (APIs), proteins, peptides, and vaccines. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a biocompatible resin composition and a method of additive manufacturing a dissolvable microneedle patch is now met by a new, useful, and nonobvious invention.

The novel biocompatible resin composition includes a backing layer that forms a base of the dissolvable microneedle patch. The backing layer includes a gripping side separated from an application side by a backing layer height. A microneedle applicator including a base is secured to the application side of the backing layer. The microneedle applicator extends in a direction away from the application side of the backing layer to a tip. The tip includes a diameter than is smaller than a diameter of the base. In an embodiment, the microneedle applicator includes an applicator height defined by a distance between the base and the tip, with a ratio of the backing layer height to the applicator height being at least 4:1.

The backing layer and the microneedle applicator are each formed from a biocompatible resin composition. The biocompatible resin composition includes lithium phenyl-2,4,6-trimethylbenzoylphospinate of between 0.225 and 0.75% (w/w), water of between 4 and 30% (w/w), and poly(ethylene glycol) diacrylate of between 61 and 84% (w/w). In an embodiment, the biocompatible resin composition includes an amount of methacrylated hyaluronic acid of between 0.25 and 0.75% (w/w).

In an embodiment, the microneedle applicator is one of a plurality of microneedle applicators that are arranged in a microneedle applicator array. In the array, each of the plurality of microneedle applicators includes an equal shape, size, area, and volume. In an embodiment, each of the plurality of microneedle applicators is spaced apart from an adjacent one of the plurality of microneedle applicators by an equal distance.

The dissolvable microneedle patch is configured to deliver an amount of a therapeutic to a subject through a transdermal application. As such, the dissolvable microneedle patch is configured to secure to an outer layer of skin of a subject with the microneedle applicator being disposed adjacent to the outer layer of skin and the tip being inserted beneath the outer layer of skin, such that the amount of the therapeutic is configured to transfer from the dissolvable microneedle patch to the subject via the tip. In an embodiment, the biocompatible resin composition includes the amount of the therapeutic impregnated therein. For example, an embodiment of the biocompatible resin composition includes an amount of verapamil hydrochloride of between 1.5 and 2% (w/w). In another embodiment, the biocompatible resin composition includes an amount of ibuprofen of 8%.

A novel method of additive manufacturing a dissolvable microneedle patch includes a step of mixing an amount of lithium phenyl-2,4,6-trimethylbenzoylphophinate with an amount of water to form a first solution. The first solution is mixed with an amount of poly(ethylene glycol) diacrylate to form a second solution. The method includes a step of isolating a supernatant of the second solution by spinning the second solution in a centrifuge, forming a biocompatible resin composition. The biocompatible resin composition is used as an input material for an additive manufacturing machine. The method further includes the step of instructing the additive manufacturing machine to create a dissolvable microneedle patch from the biocompatible resin composition. In an embodiment, the method includes a step of curing the dissolvable microneedle patch after the step of additive manufacturing the dissolvable microneedle patch by disposing the dissolvable microneedle patch in an ultraviolet curing chamber and subjecting the dissolvable microneedle patch to a temperature of 60° C.

In an embodiment, the step of forming the first solution further includes the step of mixing an amount of methacrylated hyaluronic acid to the amount of lithium phenyl-2,4,6-trimethylbenzoylphophinate and the amount of water. The amount of the lithium phenyl-2,4,6-trimethylbenzoylphophinate is between 0.225 and 0.75% (w/w), and the amount of the methacrylated hyaluronic acid is between 0.25 and 0.75% (w/w). In an embodiment including the methacrylated hyaluronic acid, the second solution is heated to evaporate at least a portion of the amount of water, such that the amount of water in the heated second solution is less than 4% (w/w).

In an embodiment, the step of forming the first solution further includes the step of mixing an amount of a therapeutic, such as verapamil hydrochloride, to the amount of lithium phenyl-2,4,6-trimethylbenzoylphophinate and the amount of water. The amount of the verapamil hydrochloride is between 1.5 and 2% (w/w). In an embodiment, the therapeutic is ibuprofen in the amount of 8% (w/w). In an embodiment, the therapeutic is configured to be released to a subject using the dissolvable microneedle patch over a period of 3 days to 7 days.

An object of the invention is to improve the stability and efficiency of additive manufactured dissolvable microneedle applicators such that therapeutics can be effectively delivered through the creation of microscopic pathways beneath the outer surface of skin.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 2 depicts a table of biocompatible resin batches for printing dissolvable microneedles showing with varying compositions of poly(ethylene glycol) diacrylate (PEGDAMA) with methacrylated hyaluronic acid (Me HA), lithium phenyl-2,4,6-trimethylbenzoylphosphinate (LAP), and water.

FIG. 5 depicts a table of biocompatible resin batches for printing dissolvable microneedles showing with varying compositions of poly(ethylene glycol) diacrylate (PEGDAMA) with ibuprofen, lithium phenyl-2,4,6-trimethylbenzoylphosphinate (LAP), and water.

FIG. 11 depicts a table of the flux of a therapeutic in an ex vivo study using a microneedle patch having 0.225% (w/w) of LAP and 10% (w/w) of water, in accordance with an embodiment of the present invention.

DETAILED DESCRIPTION OF THE INVENTION

Figure 1:
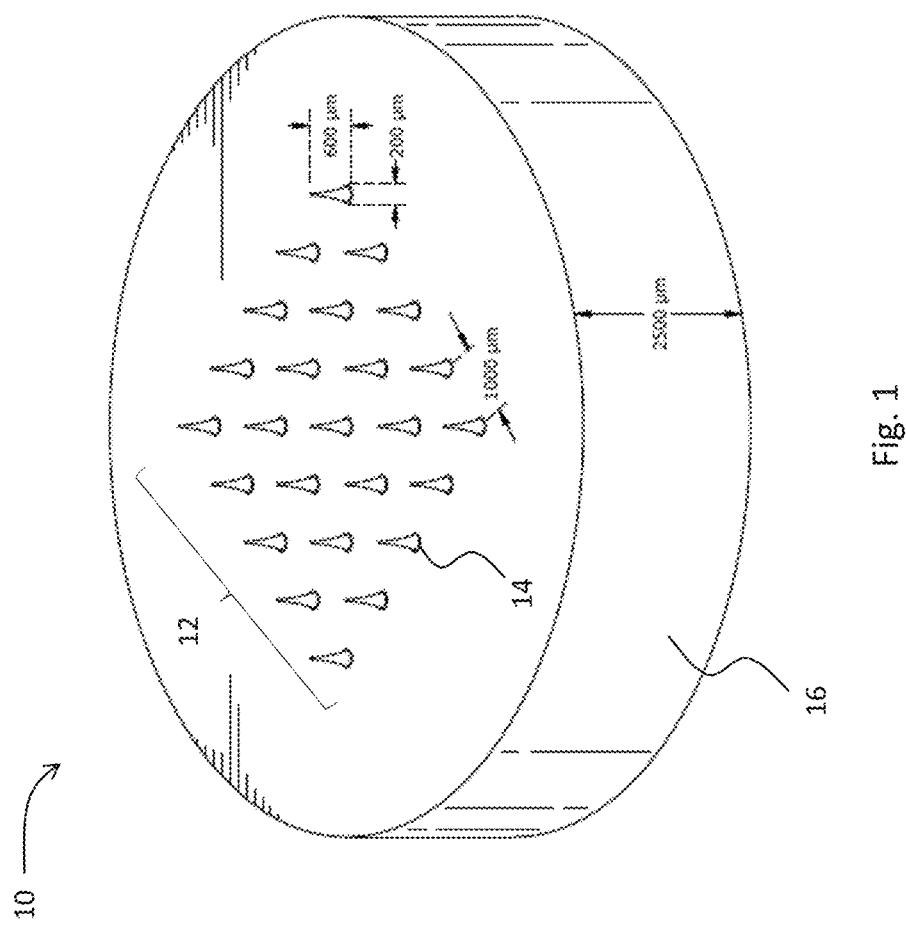
FIG. 1 depicts an embodiment of a microneedle patch including an array of microneedle applicators, in accordance with an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about." As used herein, "about" or "approximately" refers to being within an acceptable error range for the particular value as determined by one of ordinary skill in the art, which will depend in part on how the value is measured or determined. As used herein, the term "about" refers to ±10% of the numerical; it should be understood that a numerical including an associated range with a lower boundary of greater than zero must be a non-zero numerical, and the term "about" should be understood to include only non-zero values in such scenarios.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value.

Furthermore, such an interpretation should apply regardless of the range or the characteristics being described.

As used herein, "subject" is used to describe a human or other animal to whom treatment is administered, including prophylactic treatment with the compositions of the present invention.

As used herein, the term "pharmaceutically acceptable carrier" is used to describe any of the standard pharmaceutically acceptable carriers. The pharmaceutically acceptable carrier can include excipients such as diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils.

Any of the compositions disclosed herein may be administered with or without an excipient. Excipients include, for example, encapsulating materials or additives such as release modifying agents; efficacy enhancing agents; absorption accelerators; antioxidants; binders; buffers; coating agents; pigments; diluents; disintegrating agents; emulsifiers; extenders; fillers; flavoring agents; humectants; lubricants; preservatives; sterilizing agents; solubilizers; wetting agents; and mixtures thereof.

As used herein, "administering" or "administration" refers to the process by which the compositions of the present invention are delivered to a subject for treatment purposes. The compositions of the present invention may be administered topically to the subject in dosage unit formulations containing conventional nontoxic pharmaceutically acceptable carriers, adjuvants, and vehicles as desired. Administration may occur once or multiple times.

"Preventing" or "prevention" as used herein refers to any of: halting the effects of infection or pain, reducing the effects of infection or pain, reducing the incidence of infection or pain, reducing the development of infection or pain, delaying the onset of symptoms of infection or pain, increasing the time to onset of symptoms of infection or pain, and reducing the risk of development of infection or pain.

"Treatment" or "treating" as used herein refers to any of: the alleviation, amelioration, elimination and/or stabilization of a symptom or characteristic, as well as delay in progression of a symptom of a particular disease, such as cancer, arthritis, and high blood pressure, as well as in the delivery of vaccinations designed to prevent or decrease a likelihood of an onset of a symptom, characteristic, or progression of a symptom of a particular disease. For example, "treatment" of an antimicrobial infection may include any one or more of the following: amelioration and/or elimination of one or more symptoms/characteristics associated with antimicrobial infections, reduction of one or more symptoms/characteristics of antimicrobial infections, stabilization of symptoms/characteristics of antimicrobial infections, and delay in progression of one or more symptoms/characteristics of antimicrobial infections.

As used herein, the term "therapeutically effective amount" is determined based on such considerations as known in the art including the recipient of the treatment, the recipient's tolerance for the compound, the disease being treated, the severity of the disease being treated, the composition containing the active agent, the time of administration, the route of administration, the duration of treatment, the potency of the active agent, the bioavailability of the active agent, the rate of clearance of the active agent from the subject, and whether or not another active agent is co-administered. The amount of the active agent of the instant invention that may be administered to a subject must be effective to achieve a beneficial or desired response, including but not limited to, any one or more of: improved survival rate, more rapid recovery, and improvement or elimination of symptoms associated with antimicrobial infections. In accordance with the present invention, a suitable single dose size is a dose that is capable of preventing or alleviating (reducing or eliminating) a symptom in a subject when administered one or more times over a suitable time period. One of ordinary skill in the art can readily determine appropriate single dose amounts for systemic administration based on the size of the animal and the route of administration.

"Infection" as used herein refers to the invasion of one or more microorganisms such as bacteria, viruses, fungi, yeast or parasites in the body of a subject in which they are not normally present. "Disease" and "infection" are used interchangeably herein.

"Sustained release" as used herein refers to a composition comprising a therapeutically effective amount of the composition containing the at least one active agent, which when administered to a subject, continuously releases a stream of the at least one active agent over a predetermined period of time at a level sufficient to achieve a desired effect, such as treating infections, inflammation, or pain, throughout the predetermined time period. Reference to a continuous release stream is intended to encompass release that occurs as the result of biodegradation of the composition, or a component thereof, or as the result of metabolic transformation or dissolution of the added nutrients or other desired agents. In some embodiments, sustained release may occur from between about 3 days to about 7 days.

"Active agent" as used herein refers to a natural or synthetic substance, component or agent that has measurable specified or selective physiological activity when administered to a subject in a therapeutically effective amount. Active agents may be hydrophobic or hydrophilic. Examples of active agents as used in the present invention include antimicrobials such as antibiotics, antivirals, antifungals, antiprotozoals, and antiparasitics; antiseptics; anesthetics; and anti-inflammatories. Active agents also include beneficial compounds such as nutrients or other elements that are beneficial to the subject in that they are used by the animal to survive, grow and/or reproduce. Examples of such beneficial compounds include, but are not limited to, calcium, strontium, carbonate, magnesium, iodine/iodide, and molybdenum. At least one active agent is used in the compositions of the present invention. The at least one active agent may be present in the composition from between about 1% (w/w) to about 10% (w/w), including all values and ranges in between in 1% increments. In some embodiments, multiple active agents are used with such agents being released simultaneously or sequentially.

The present invention includes a biocompatible resin composition that is used in the manufacture of a dissolvable microneedle patch that is used for the transdermal delivery of one or more active pharmaceutical ingredients (API's), proteins, and peptides to a subject. The microneedles are formulated using a continuous, one-step process utilizing 3D printing technology, thereby employing a highly efficient and reproducible technique as compared to the prior art of micromolding techniques. Once manufactured, the microneedle patches are formulated to adhere to an outer layer of a subject's skin. Once administered to the subject, the microneedle compositions create microscopic pathways into the subject's subdermal layers to deliver one or more active agents to the subject, such as to the subject's bloodstream.

As noted above, the biocompatible resin composition is used in the additive manufacturing of a microneedle patch for efficient therapeutic delivery via one or more microneedle applicators. An example of microneedle patch 10 is shown in FIG. 1, including microneedle array 12 having twenty-five (25) individual microneedle applicators 14. In the embodiment shown in FIG. 1, each microneedle applicator 14 is approximately equal in area, volume, and shape, with each microneedle applicator 14 having a height of approximately 600 μm and a base diameter of approximately 200 μm. In addition, in an embodiment, each microneedle applicator 14 is substantially equally spaced apart from an adjacent microneedle applicator 14, such that a uniform distribution of therapeutics is achieved when the applicators 14 are attached to a subject's outer layer of skin. For example, in the embodiment shown in FIG. 1, each microneedle applicator 14 is spaced apart from an adjacent microneedle applicator 14 by a distance of approximately 1,000 μm. It should be appreciated that embodiments of the microneedle patch 10 can include a single microneedle applicator 14 without array 12, and that embodiments of the microneedle patch 10 can include more than or fewer than 25 individual microneedle applicators 14. Moreover, it should be appreciated that microneedle applicators 14 can vary in area and volume, and that targeted arrangements of microneedle applicators 14 can result in non-uniformly spaced apart applicators.

The one or more microneedle applicators 14 are arranged on backing layer 16 that provides a structural support for the microneedle applicator(s) 14. Accordingly, backing layer 16 has a greater area and a greater volume as compared to a collective area and volume of the one or more microneedle applicators 14, such that the one or more microneedle applicators 14 are housed on backing layer 16. In an embodiment, backing layer 16 includes a height of approximately 1,500-2,500 μm.

After printing via an additive manufacturing machine, the resulting microneedle patch was then washed in 70% isopropyl alcohol (IPA) to clean any excess resin from the printed microneedle patch 10. In an embodiment, in which microneedle patch 10 is additive manufactured from a stereolithography apparatus (SLA) process, the microneedle patch 10 is cured in an ultraviolet (UV) curing chamber for 15 minutes at C to harden patch 10, thereby solidifying the structure of patch 10 for use in a therapeutic treatment application. In another embodiment, in which microneedle patch is additive manufactured from a digital light process (DLP), the microneedle patch is cured in an ultraviolet (UV) curing chamber for 5 minutes at 23° C. to harden patch thereby solidifying the structure of patch 10 for use in a therapeutic treatment application.

Example 1

As shown in the table of FIG. 2, various batches of biocompatible resin compositions (A1-A7) were formulated to assess the effectiveness of each resin composition for use in additive manufacturing, via stereolithography apparatus (SLA) processes, to create dissolvable microneedle patches 10 and microneedle applicators 14 as described in detail above. Two of the experimental batches, A1 and A2, included the direct addition of lithium phenyl-2,4,6-trimethylbenzoylphophinate (LAP) to poly(ethylene glycol) diacrylate (PEGDAMA) without the use of methacrylated hyaluronic acid (Me HA), water, or other materials in the composition. For experimental batches A3 and A4, LAP was first dissolved in water prior to being added to PEGDAMA. Similarly, for experimental batches A5, A6, and A7, LAP and Me HA were added to water prior to being added to PEGDAMA.

It was found that a final concentration of water of 4% or greater (w/w) results in a resin that yields unstable microneedles and associated structures created via stereolithography apparatus (SLA) processes. Accordingly, after mixing with PEGDAMA, the resulting composition for each batch was heated to a temperature of approximately 42° C. to achieve an evaporation of fluid from the composition to form a resin that includes less than approximately 4% (w/w) of water. The resin from each batch was collected in a tube and centrifuged for approximately 5 minutes at a rate of approximately 5,000 revolutions per minute (rpm). The step of spinning the resin in a centrifuge was performed to eliminate any undissolved particles from each batch. After centrifuging, the clear supernatant from each batch was isolated and saved for use as the final resin for use in an additive manufacturing process to create a microneedle patch (described in greater detail below).

Overall, the resins formed from batches A1 and A2 showed that LAP did not solubilize when mixed directly with PEGDAMA. However, for the remaining batches, A3-A7, LAP (and Me HA for batches A5-A7) completely dissolved in water and PEGDAMA, forming a clear, transparent, biocompatible resin composition for use during additive manufacturing processes to create a therapeutic delivery device, such as a microneedle patch.

In various embodiments, one or more substances, including API's, proteins, peptides, and vaccines may be combined with the biocompatible resin composition, depending on the desired therapeutic delivery device. Depending on the particular API and the required dose, it should be appreciated that various % (w/w) of the API can be used, depending on the desired dosage. For example, in an embodiment, an exemplary solution containing about 0.75% (w/w) Me HA, about 0.75% (w/w) LAP, and about 1.8% (w/w) of Verapamil Hydrocloride (Verapamil HCL) was dissolved in water. The solution was then slowly added to a beaker containing a prepolymer solution, such as PEGDAMA, to form an initial composition, as noted in the sections above.

Example 1—Results

Figure 3A:
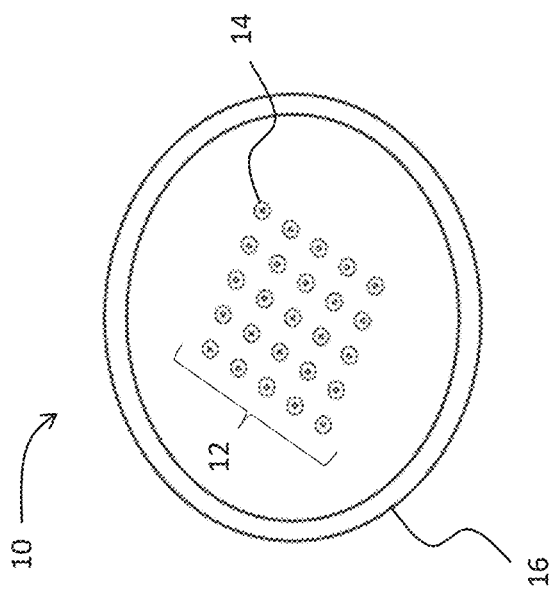
FIG. 3A depicts an embodiment of a microneedle patch including an array of microneedle applicators printed on a backing layer, in accordance with an embodiment of the present invention.
Figure 3B:
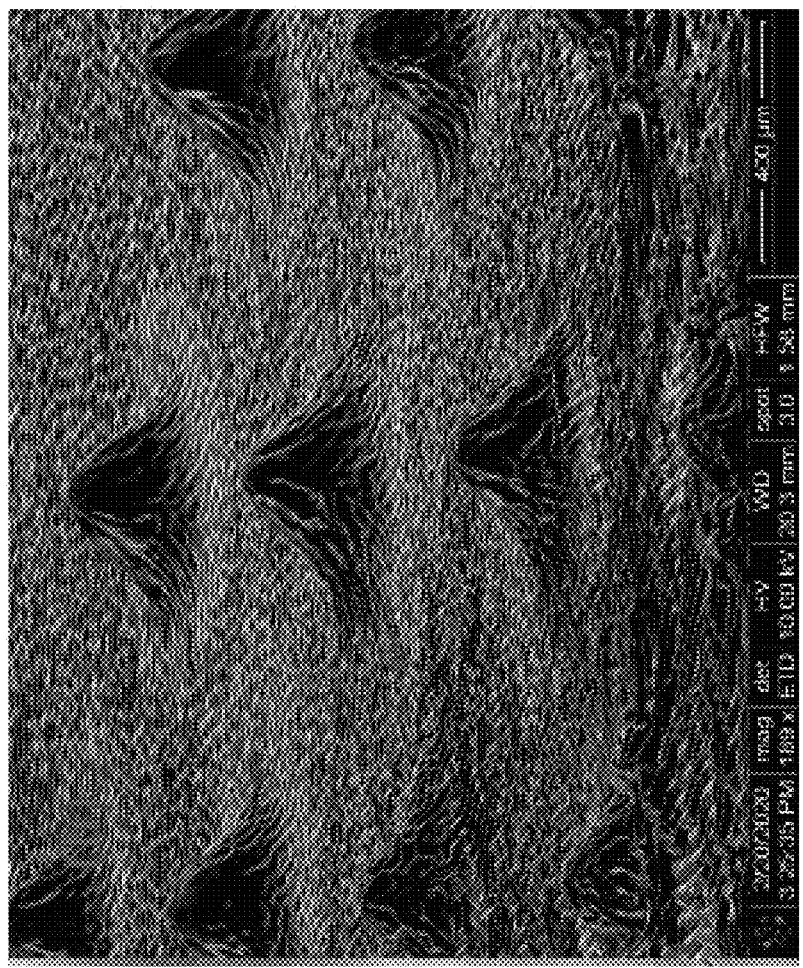
FIG. 3B depicts a scanning electron microscope (SEM) image of an embodiment of a microneedle patch showing a close-up view of an array of microneedle applicators, in accordance with an embodiment of the present invention.
Figure 4:
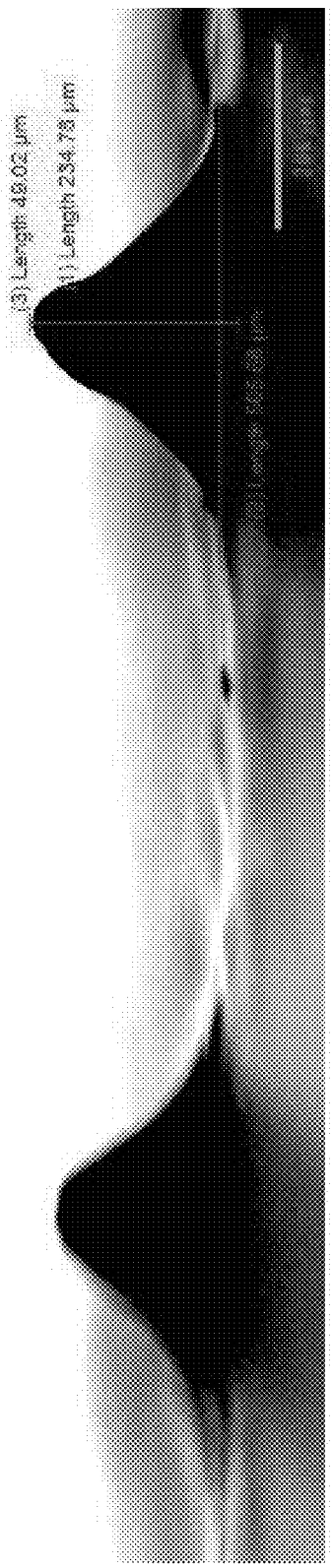
FIG. 4 depicts a microscopic image of an embodiment of a microneedle patch showing a close-up view of adjacent microneedle applicators of the microneedle patch, in accordance with an embodiment of the present invention.

The compositions formed in batches A1-A4 and printed in accordance with the additive manufacturing and curing steps outlined above were unable to polymerize and did not produce microneedle patches having sufficient structural integrity due, in part, to the lack of Me HA in the compositions. In addition, the compositions formed in batches A5-A6 containing Me HA were able to polymerize and print backing layer 16 of microneedle patches 10, but not microneedle applicator(s) 14 themselves. However, the composition formed in batch A7, containing a higher concentration of LAP and Me HA (w/w), was able to polymerize and print both backing layer 16 and microneedle applicators 14. An embodiment of the resulting microneedle patch 10, including backing layer 16 and microneedle applicators 14, is depicted in FIGS. 3A and 3B, which includes individual microneedle applicators 14 having a height of approximately 400 μm, a base diameter of approximately 370 μm, and a tip diameter of approximately 55 μm. An alternative embodiment of microneedle patch 10 is shown in FIG. 4, including one or more individual microneedle applicators 14 having a height of approximately 235 μm, base diameter of approximately 500 μm, and a tip diameter of approximately 50 μm.

Moreover, in embodiments in which microneedle patches 10 are associated with one or more API, such as Verapamil HCL, the API can be applied to the surface of one or more of microneedle applicators 14 after the additive manufacturing process, or can be added to the LAP prior to mixing with PEGDAMA. As such, the API can be introduced into the body via microscopic channels formed within the subject's skin when microneedle applicator(s) 14 contacts the subject's skin, thereby penetrating the outer surface of the subject's skin.

Example 2

Similarly, as shown in the table of FIG. 5, various batches of biocompatible resin compositions (B1-B9) were formulated to assess the effectiveness of each resin composition for use in additive manufacturing processes, via digital light process (DLP), to create dissolvable microneedle patches 10 and microneedle applicators 14 as described in detail above. For each experimental batch, the concentration of ibuprofen remained constant at 8% (w/w); however, the concentrations of LAP, water, and PEGDAMA varied with each batch. Specifically for LAP, in batches B1-B3, the concentration of LAP remained constant at 0.225% (w/w); in batches B4-B6, the concentration of LAP remained constant at 0.49% (w/w); and in batches B7-B9, the concentration of LAP remained constant at 0.75% (w/w). Similarly, in batches B1, B4, and B7, the concentration of water was 10% (w/w); for batches B2, B5, and B8, the concentration of water was 20% (w/w); and for batches B3, B6, and B9, the concentration of water was 30% (w/w). The concentration of PEGDAMA depended on the concentrations of the LAP, ibuprofen, and water, as shown in FIG. 5. Results show that a greater concentration of water results in an increased release of therapeutic from a resulting microneedle patch 10.

To form the batches, LAP was first dissolved in water in the w/w concentrations shown in FIG. 5. The resulting solution was then mixed with PEGDAMA (molecular weight 550) and vortexed for 1 minute. For batches B4 and B7, the initial concentration of water was 20%; after mixing with PEGDAMA, the solutions were heated to a temperature of approximately 42° C., with constant stirring for approximately 45-60 minutes, to achieve an evaporation of water to reach a final concentration of 10% water (w/w). Next, ibuprofen is mixed to the resulting solution and is vortexed until the ibuprofen concentration completely dissolves in the resulting resin.

Results—Example 2

Figure 6A:
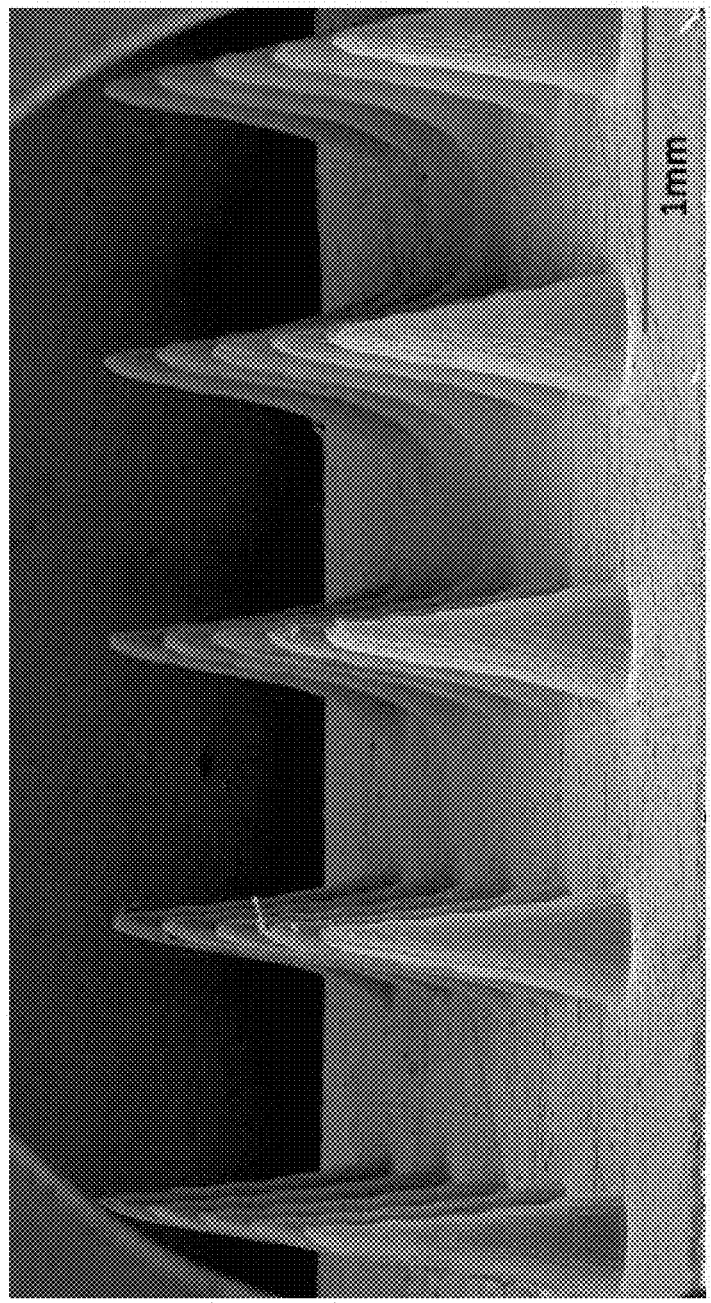
FIG. 6A depicts a SEM image of an embodiment of a microneedle patch having 0.75% (w/w) LAP and 10% (w/w) water, in accordance with an embodiment of the present invention.
Figure 6B:
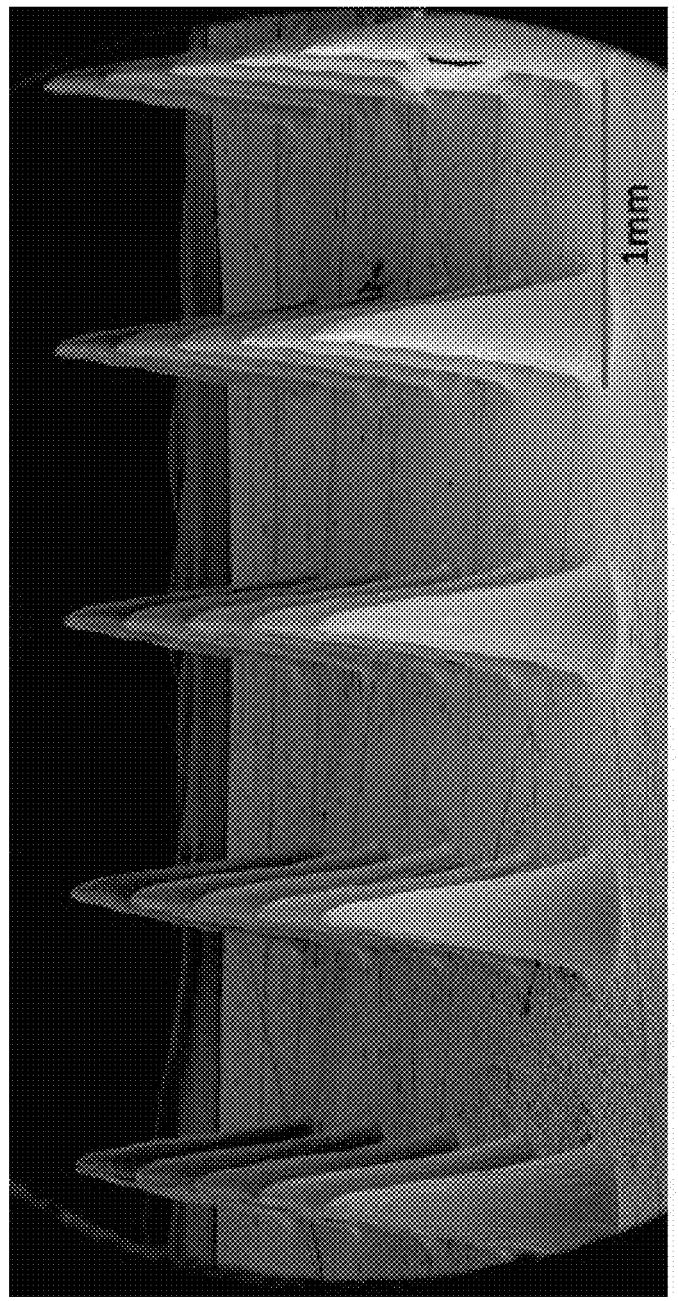
FIG. 6B depicts a SEM image of an embodiment of a microneedle patch having 0.49% (w/w) LAP and 10% (w/w) water, in accordance with an embodiment of the present invention.
Figure 6C:
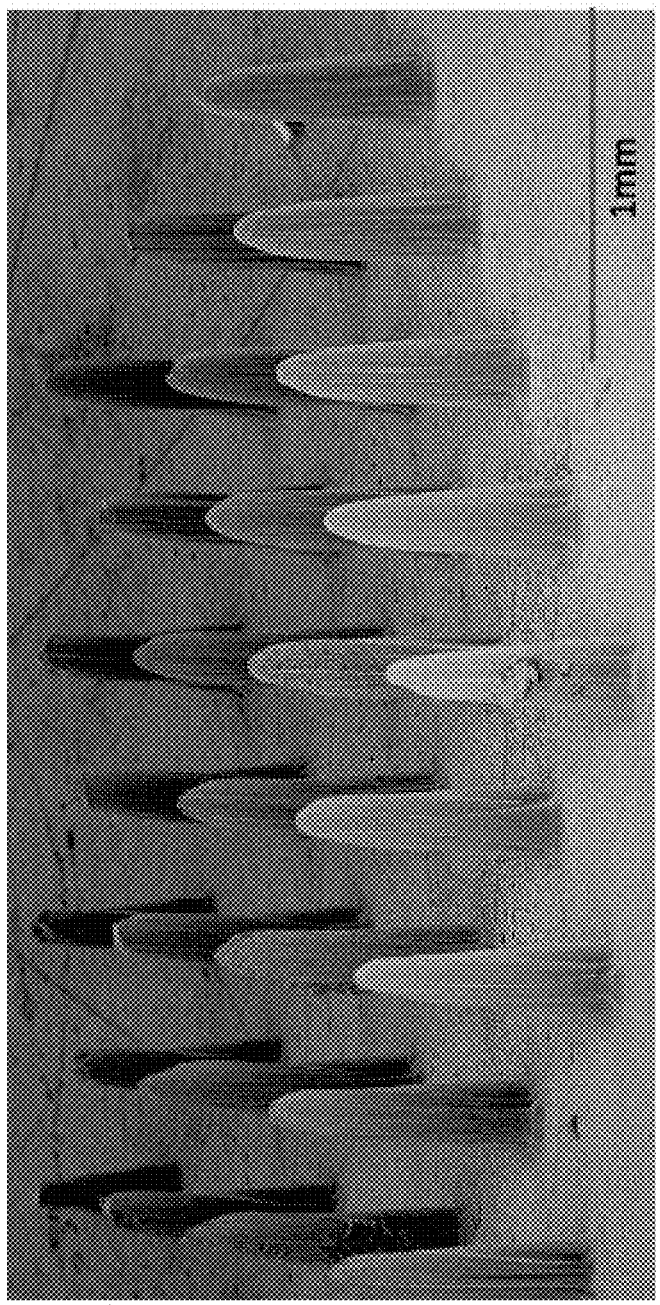
FIG. 6C depicts a SEM image of an embodiment of a microneedle patch having 0.225% (w/w) LAP and 10% (w/w) water, in accordance with an embodiment of the present invention.
Figure 7:
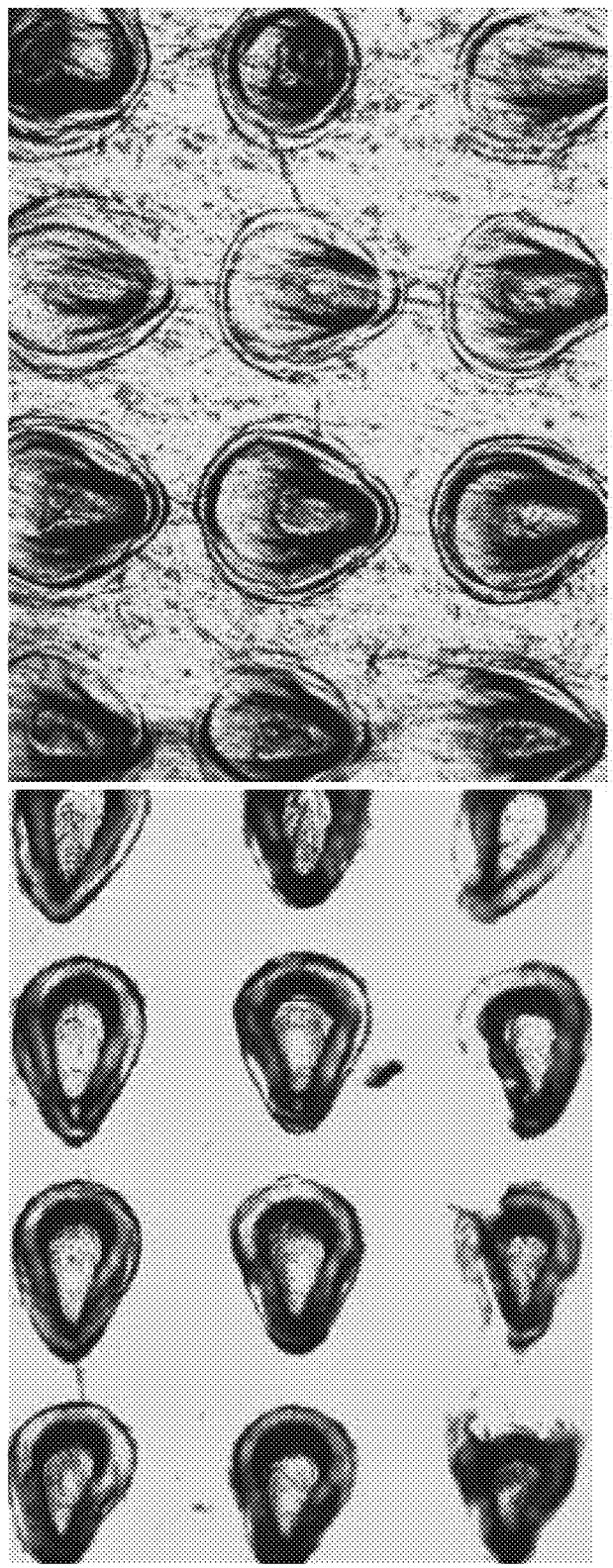
FIG. 7 depicts optical microscope images of two layers of a parafilm after applying an embodiment of a microneedle patch thereto, showing the formation of pores within the layers of the parafilm, in accordance with an embodiment of the present invention.

As shown in FIGS. 6A-6C, microneedle patches 10 as described above are additive manufactured in accordance with the concentrations of components shown in FIG. 5. The microneedle patches 10 as shown in FIG. 6A include 0.75% (w/w) LAP and 10% (w/w) water; the microneedle patches 10 as shown in FIG. 6B include 0.49% (w/w) LAP and 10% (w/w) water; the microneedle patches 10 as shown in FIG. 6C include 0.225% (w/w) LAP and 10% (w/w) water. Layers of parafilm were treated by the microneedle patches and observed under an optical microscope to study the mechanical properties of the needles. The mechanical uniformity of microneedles was estimated from the dimensions of the pores in the first layer and the number of pores in the last layer. As shown in FIG. 7, the results showed that, after applying the microneedle patches 10 on the parafilm layers, conical pores formed in both the first and second layer of the parafilm. Moreover, pores were observed on the third layer of parafilm, with indentations being formed in the fourth layer of parafilm. The pores formed on the parafilm were distinct and uniform in shape and size, making the microneedle patches 10 strong enough to break through the epidermal layer of skin of a subject.

Figure 8:
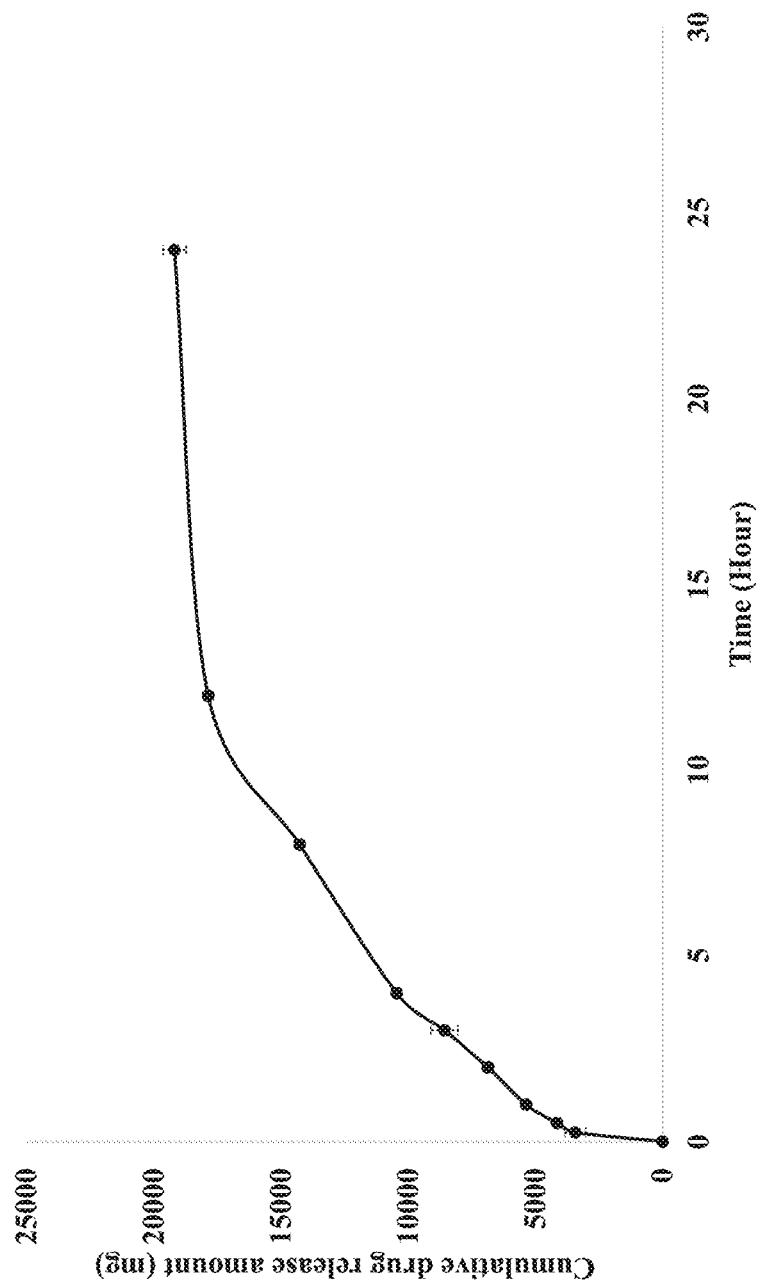
FIG. 8 graphically depicts therapeutic release rates over time using a microneedle patch, in accordance with an embodiment of the present invention.

In addition, an in-vitro drug release study was performed in a release media (phosphate buffer (pH 7.4) with 25% ethanol and 5% polysorbate 80). A microneedle patch 10 having a 7×7 microneedle array 12 with 0.225% (w/w) LAP and 10% (w/w) water was added in 20 mL of the release media in a beaker and placed on a magnetic hot plate with 350 revolutions per minute speed at a temperature of 37° C. Samples were taken at time intervals of 1, 2, 3, 4, 8, 12, and 24 hours. At each sampling time, a fresh 20 mL of phosphate buffer was replaced in the beaker. Further, all the samples were analyzed using high-performance liquid chromatography (HPLC) with 70% acetonitrile (ACN) and 30% acidified water (pH 2.5 adjusted using orthophosphoric acid), with an injection volume of 50 μm and a flow rate of 1 mL/min at 221 nm wavelength. As shown in FIG. 8, the results showed that 5 mg of ibuprofen was released from the microneedle patch in the first hour, with a steady increase in drug release up to 20 mg for 24 hours.

In addition, dermatomed human skin (0.5±0.1 mm thickness) was used for a permeation study. The microneedle patch 10 described in the previous study (0.225% (w/w) LAP and 10% (w/w) water) was placed on the dermatomed human skin and retained thereon using an adhesive to maintain contact between the patch 10 and the skin. The microneedle patch 10 was then pressed into the dermatomed human skin for 2 minutes using a force exerted by thumb pressure. The dermatomed skin including the patch was then mounted between the donor and receiver compartments of a Franz diffusion cell. The receiver compartment included a pH 7.4 buffer with 25% ethanol and 5% polysorbate 80 and was maintained at a temperature of 32±0.5° C. with continuous stirring at 300 revolutions per minute. Samples were taken at intervals 24, 48, and 72 hours. At each sampling time, fresh receiving media was replaced in the receiving compartment. Samples were then analyzed using HPLC.

Figure 9:
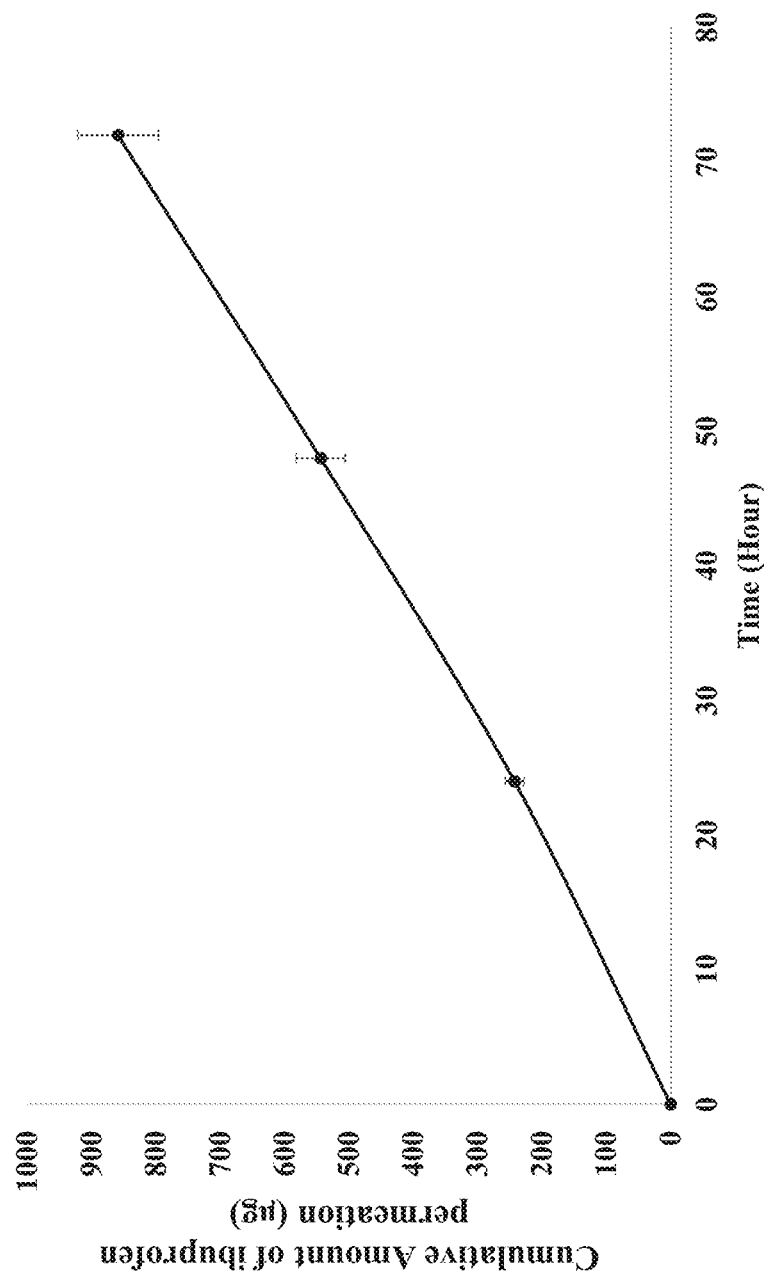
FIG. 9 graphically depicts ex vivo skin permeation over time using a microneedle patch, in accordance with an embodiment of the present invention.
Figure 10:
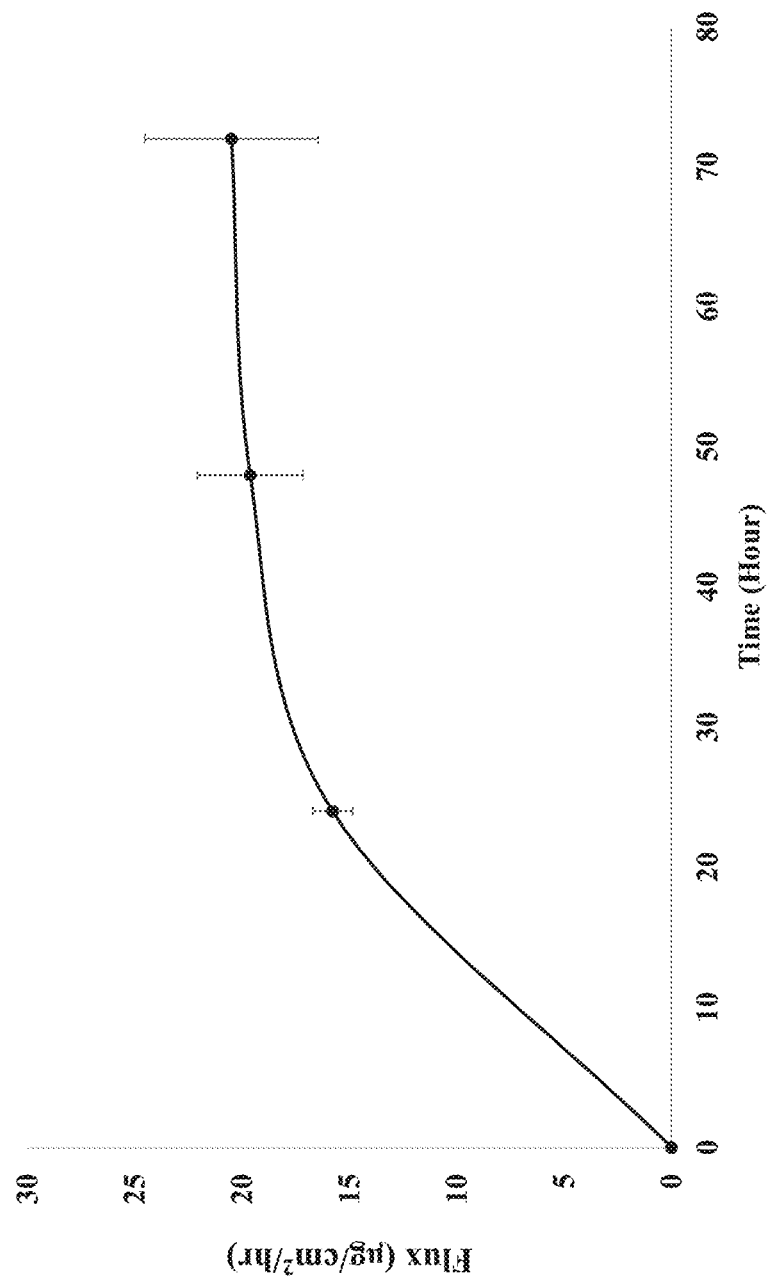
FIG. 10 graphically depicts the flux of a therapeutic in an ex vivo study using a microneedle patch, in accordance with an embodiment of the present invention.

As shown in FIG. 9, the results showed that about 900 μg (cumulative drug release) of ibuprofen was permeated from 0.64 cm 2 area at the end of 72 hours, which suggested that the microneedle patches 10 dissolved, and that the ibuprofen was released from the microneedle patches 10. As shown in FIGS. 10-11, the ibuprofen microneedle patches 10 showed flux of 15.79±0.92 (m/cm$^2$/hr) at 0-24 hours, 19.63±2.46 (m/cm$^2$/hr) at 24-48 hours and 20.50±4.05 (m/cm$^2$/hr) at 48-72 hours. Moreover, Table 1 below shows the settings of an additive manufacturing device printing the microneedle patches 10 including ibuprofen.

TABLE 1

Settings of the DLP additive manufacturing device printing the Ibuprofen microneedle patches, showing the change in exposure time and LED currents depending on the layers of the microneedles being printed

| From layer | To layer | Exposure time (Seconds) | The LED Current (5.86 mA/unit) | Printing temperature |
|---|---|---|---|---|
| 1 | 1 | 8 | 125 to 150 | 37° C. |
| 2 | 5 | 6 | | |
| 6 | 100 | 4 | | |
| 101 | 155 | 1.5 to 8 | | |
| 156 | 160 | 1.5 to 8 | | |

REFERENCES

[1] Van Landuyt, K. L., et al., *Evaluation of cell responses toward adhesives with different photoinitiating systems*. Dental materials, 2015. 31(8): p. 916-927.
[2] Fairbanks, B. D., et al., *Photoinitiated polymerization of PEG-diacrylate with lithium phenyl-2, 4, 6-trimethylbenzoylphosphinate: polymerization rate and cytocompatibility*. Biomaterials, 2009. 30(35): p. 6702-6707.
[3] Lin, H., et al., *Application of visible light-based projection stereolithography for live cell-scaffold fabrication with designed architecture*. Biomaterials, 2013. 34(2): p. 331-339.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A dissolvable microneedle patch configured to deliver an amount of a therapeutic to a subject through a transdermal application, the dissolvable microneedle patch comprising:
  a backing layer that forms a base of the dissolvable microneedle patch, the backing layer including a gripping side separated from an application side by a backing layer height, the backing layer being formed from a biocompatible resin composition, the biocompatible resin composition including lithium phenyl-2, 4,6-trimethylbenzoylphospinate of between 0.225 and 0.75% (w/w), water of between 4 and 30% (w/w), and poly(ethylene glycol) diacrylate of between 61 and 84% (w/w);
  a microneedle applicator including a base that is secured to the application side of the backing layer, the microneedle applicator extending in a direction away from the application side of the backing layer to a tip, the tip having a diameter that is smaller than a diameter of the microneedle applicator base, the microneedle applicator being formed from the biocompatible resin composition;

the amount of the therapeutic being disposed within the microneedle applicator between the microneedle applicator base and the microneedle applicator tip; and wherein the dissolvable microneedle patch is configured to secure to an outer layer of skin of a subject with the microneedle applicator being disposed adjacent to the outer layer of skin and the tip being inserted beneath the outer layer of skin, such that the amount of the therapeutic is configured to transfer from the dissolvable microneedle patch to the subject via the tip.

2. The dissolvable microneedle patch of claim 1, wherein the biocompatible resin composition further comprises methacrylated hyaluronic acid of between 0.25 and 0.75% (w/w).

3. The dissolvable microneedle patch of claim 1, wherein the biocompatible resin composition further comprises the amount of the therapeutic impregnated therein.

4. The dissolvable microneedle patch of claim 3, wherein the therapeutic is verapamil hydrochloride.

5. The dissolvable microneedle patch of claim 4, wherein the amount of the verapamil hydrochloride is between 1.5 and 2% (w/w).

6. The dissolvable microneedle patch of claim 3, wherein the therapeutic is ibuprofen, wherein the amount of the ibuprofen is 8% (w/w).

7. The dissolvable microneedle patch of claim 1, wherein the microneedle applicator is one of a plurality of microneedle applicators that are arranged in a microneedle applicator array, wherein each of the plurality of microneedle applicators is spaced apart from an adjacent one of the plurality of microneedle applicators by an equal distance.

8. The dissolvable microneedle patch of claim 7, wherein each of the plurality of microneedle applicators includes an equal shape, size, area, and volume.

9. The dissolvable microneedle patch of claim 1, wherein the microneedle applicator includes an applicator height defined by a distance between the microneedle applicator base and the microneedle applicator tip, wherein a ratio of the backing layer height to the applicator height is at least 4:1.

* * * * *